United States Patent [19]

Moore et al.

[11] 3,978,850

[45] Sept. 7, 1976

[54] MEDICAL DIAGNOSTIC INSTRUMENTS

[75] Inventors: William C. Moore, Skaneateles; Richard W. Newman, Auburn, both of N.Y.

[73] Assignee: Welch Allyn, Inc., Skaneateles Falls, N.Y.

[22] Filed: Mar. 24, 1975

[21] Appl. No.: 561,308

[52] U.S. Cl............................... 128/9; 128/23
[51] Int. Cl.²........................................ A61B 1/22
[58] Field of Search.................. 128/22, 23, 3–18; 240/2 MA, 10.6 R, 10.61, 41.5, DIG. 8

[56] References Cited
UNITED STATES PATENTS

| | | | |
|---|---|---|---|
| 2,365,104 | 12/1944 | Peck et al. | 128/9 |
| 3,698,387 | 10/1972 | Moore et al. | 128/9 |
| 3,760,798 | 9/1973 | Eoinger | 128/6 |
| 3,812,847 | 5/1974 | Moore et al. | 128/9 |
| 3,874,371 | 4/1975 | Stader | 128/9 |

*Primary Examiner*—Robert W. Michell
*Assistant Examiner*—Henry S. Layton
*Attorney, Agent, or Firm*—Bruns & Jenney

[57] ABSTRACT

A novel construction for electrically illuminated medical diagnostic instruments, particularly otoscopes and ophthalmoscopes. The invention fills a need for instruments that are relatively low cost and yet of good quality, the lower cost being achieved in part by the materials used and in part by the ease with which the components can be assembled. In addition to being economical, the instruments disclosed are easy to use and maintain. They are lightweight and compact, and for ease of maintenance are provided with an easily removable light source unit in which the lamp and batteries are mounted. This greatly facilitates changing these expendable items when such becomes necessary.

6 Claims, 19 Drawing Figures

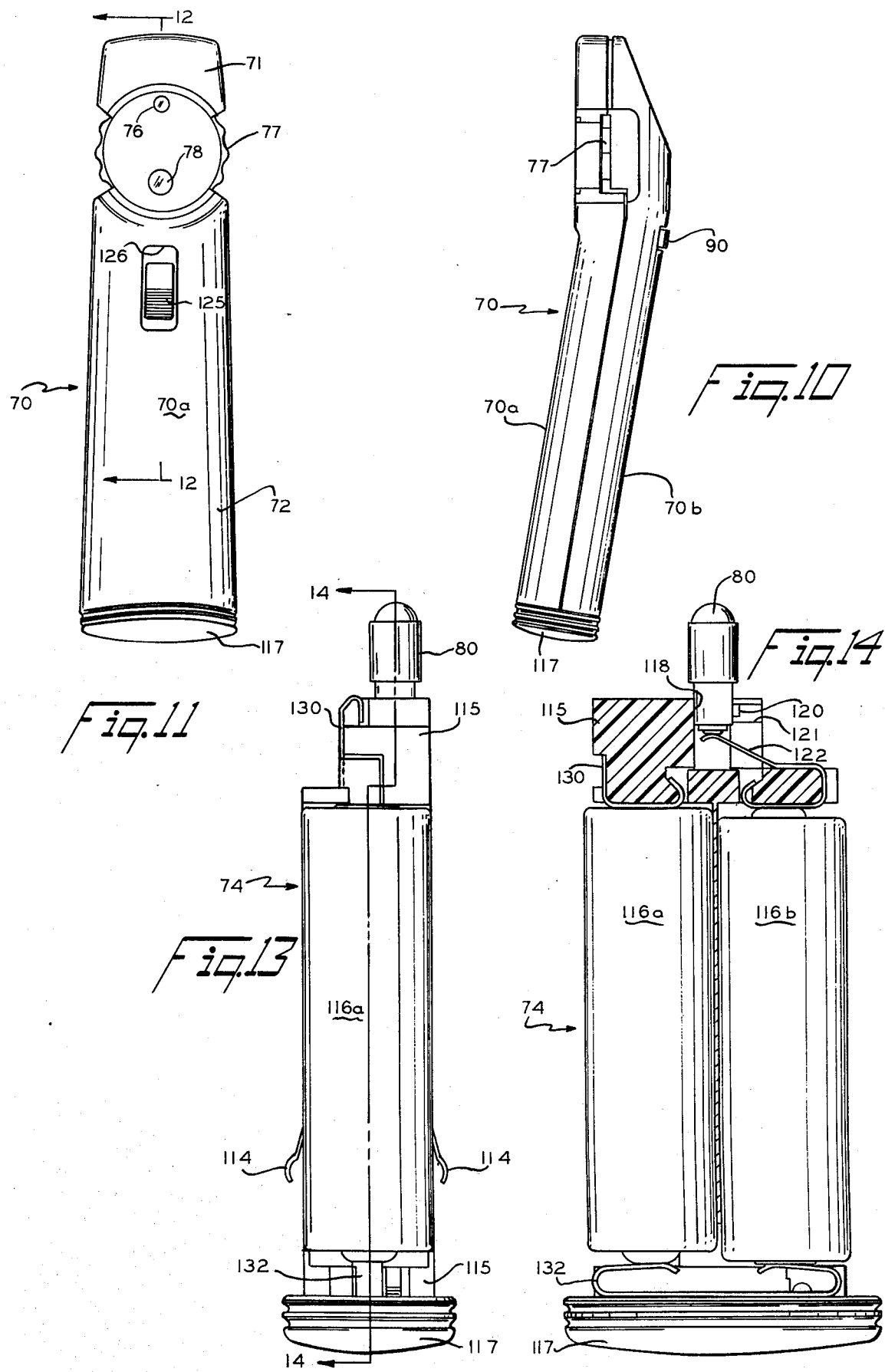

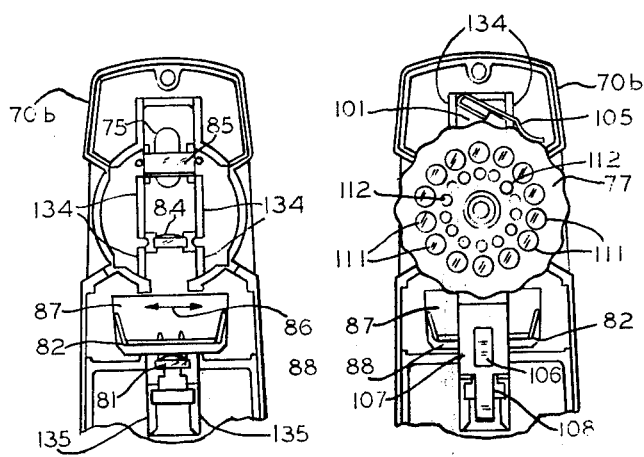
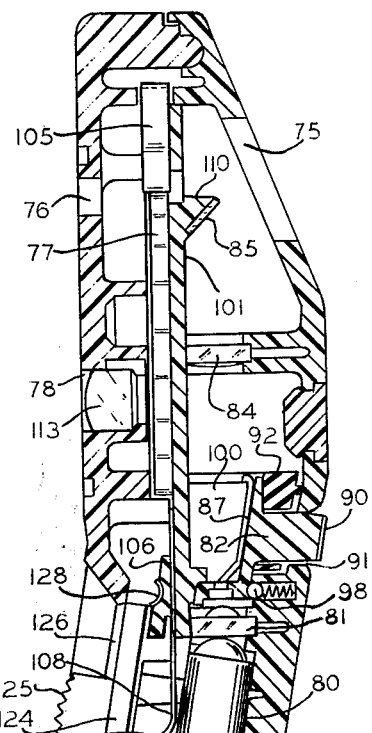
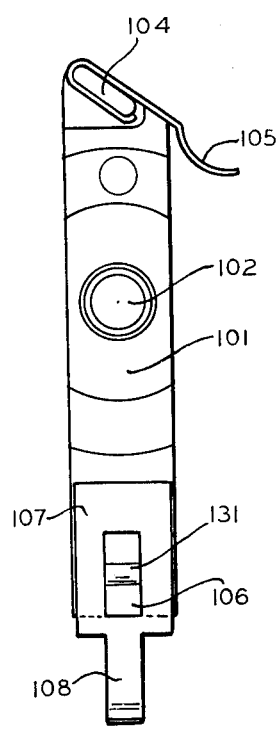
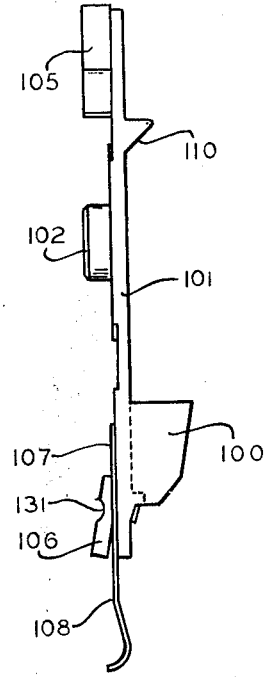
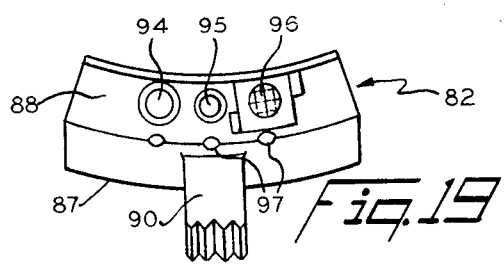

MEDICAL DIAGNOSTIC INSTRUMENTS

BACKGROUND OF THE INVENTION

This invention relates generally to medical instruments, and has particular reference to a novel construction for electrically illuminated diagnostic instruments such as otoscopes and ophthalmoscopes.

Heretofore, medical diagnostic instruments such as otoscopes and ophthalmoscopes have usually been built for durability as well as quality and to this end have been constructed with precisely machined stainless steel and/or chrome plated parts and high grade optical components. However, with the ever increasing costs of labor and materials, the cost of manufacturing instruments of this type has also increased substantially making it desirable to make available less expensive instruments without seriously sacrificing quality.

Beyond the cost consideration, a disadvantage of the prior art instruments has been that they usually are constructed so as to discourage disassembly or tinkering by the physician or his nurse. This has resulted in many instances in making it difficult to even change the lamp or a battery.

SUMMARY OF THE INVENTION

The medical instrument construction disclosed herein is particularly for otoscopes and ophthalmoscopes although it will be apparent as the description proceeds that features of the invention can be advantageously utilized in other instruments also.

The principal objective of the invention is to provide electrically illuminated diagnostic instruments that are relatively low cost and yet of good quality. The lower cost is achieved through use of less expensive metals and by simplifying the assembly of the instruments. Thus, the instruments are made of molded plastic components, including the optical components, and during assembly these components, to a large degree are simply dropped in position. Good quality, however, is maintained by holding close tolerances and insuring proper alignment of the optical components.

Another important objective of the invention is to provide medical diagnostic instruments that are easy to use and maintain. To this end, the instruments are lightweight and compact, and for ease of maintenance they are provided with an easily removable light source unit in which the lamp and batteries are mounted so as to be readily accessible for changing.

BRIEF DESCRIPTION OF THE DRAWINGS

FIG. 10 is a side elevation of an ophthalmoscope embodying the construction of the invention;

FIG. 11 is a rear elevation of the ophthalmoscope of FIG. 10;

FIG. 12 is an enlarged vertical section through the ophthalmoscope taken on line 12—12 of FIG. 11;

FIG. 13 is an enlarged side elevation of the removable light source unit of the ophthalmoscope;

FIG. 14 is a vertical section through the light source unit taken on line 14—14 of FIG. 13;

FIG. 15 is a fragmentary elevation of the interior of the head portion of the ophthalmoscope showing details of the construction and assembly;

FIG. 16 is a view corresponding to FIG. 15 with additional components in position;

FIGS. 17 and 18 are back and side elevations, respectively, of the ophthalmoscope insert assembly; and FIG. 19 is a bottom perspective view of the ophthalmoscope aperture assembly.

DESCRIPTION OF THE PREFERRED EMBODIMENTS

Figure 1:
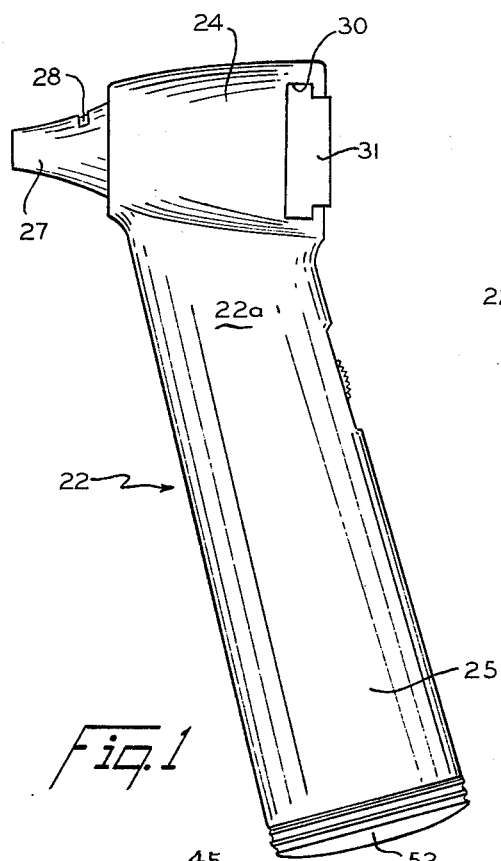
FIG. 1 is a side elevation of an otoscope embodying the construction of the invention.

Referring now to the drawings, and with particular reference to FIGS. 1–9, the otoscope embodying the invention includes an elongated hollow body, generally indicated at 22, formed of two mating halves 22a and 22b of molded plastic. The body has an upper head portion 24 and a lower handle portion 25, the handle portion being open at its lower end to allow a light source unit generally indicated at 26 to be inserted therein. The unit 26 includes the light source and power supply for the instrument as will be explained.

The head portion 24 of the instrument body has on its front or distal side a metal speculum 27 adapted to enter the ear passage of the patient. The speculum is formed with an L-shaped groove 28 for holding a disposable tip or cover (not shown) on the speculum during use, disposible covers for specula being well known in the art. On its rear or proximal side, the head portion 24 has a relatively large rectangular opening 30 in which a molded plastic lens 31 is slidably mounted essentially as described in U.S. Pat. No. 3,698,387, granted Oct. 17, 1972 to applicant W. C. Moore and another.

Figure 3:
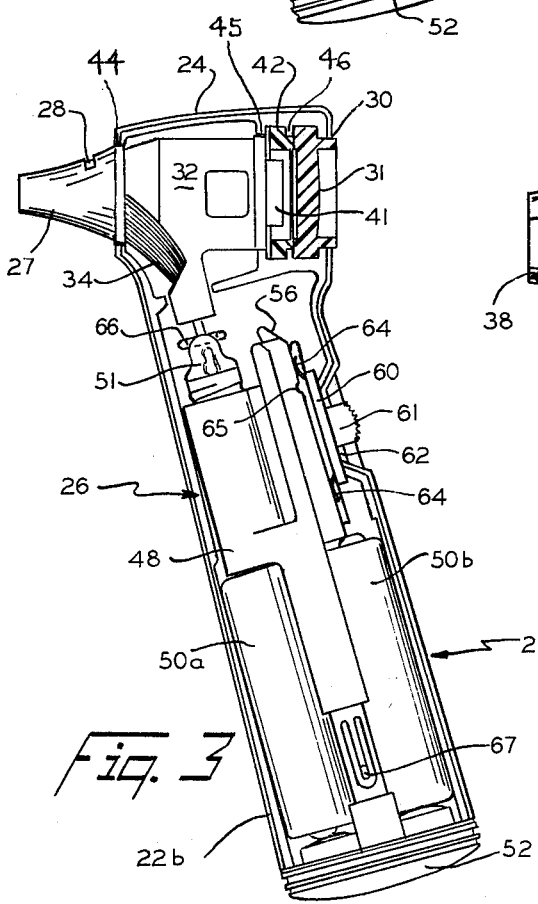
FIG. 3 is a vertical section through the otoscope taken on line 3—3 of FIG. 2.
Figure 8:
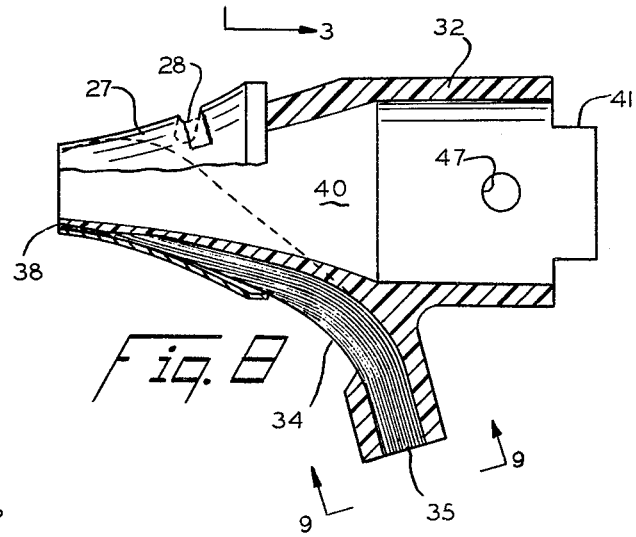
FIG. 8 is an enlarged vertical section through the speculum assembly of the otoscope with a part broken away to show the details of construction.
Figure 9:
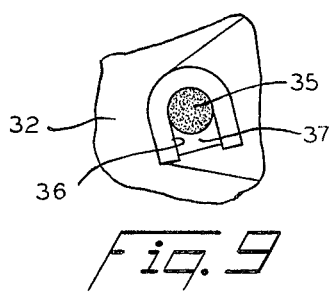
FIG. 9 is a fragmentary bottom plan view of the speculum assembly looking in the direction of arrows 9—9 of FIG. 8.

Speculum 27 forms a part of a speculum assembly, FIGS. 3 and 8, which also includes a plastic inner form 32 and a bundle 34 of clad optical fibers. At its lower end 35, the fiber optic bundle 34 is substantially cylindrical and is positioned in a channel 36 in the inner form 32, FIG. 9, the bundle being retaned in the channel by a plug 37 that is cemented in place. The distal end 38 of the inner form is essentially frusto-conical and the optical fibers fan out around this part of the form, in the space between the form and speculum 27, to form an annulus around the distil end of the viewing passage 40 that extends through the inner form. Both ends of the fiber optic bundle are ground and polished in conventional manner. The fibers are encapsulated with epoxy which holds elements 27, 32 and 37 together and prevents the fibers from being broken.

The inner form 32 has a pair of rearwardly extending lugs 41 on each side thereof and a rectangular gasket 42 of relatively soft elastomer material is mounted on these lugs as shown in FIG. 3 before the speculum assembly and gasket are positioned in one of the halves 22a, 22b of the otoscope body. In assembling the instrument, the speculum assembly and gasket are properly located in the body by means of a front opening 44 through which speculum 27 passes with a close fit and ribs or ridges 45 and 46 that are molded in the interiors of the body halves and respectively locate rear end of inner form 32 and the gasket 42.

Figure 2:
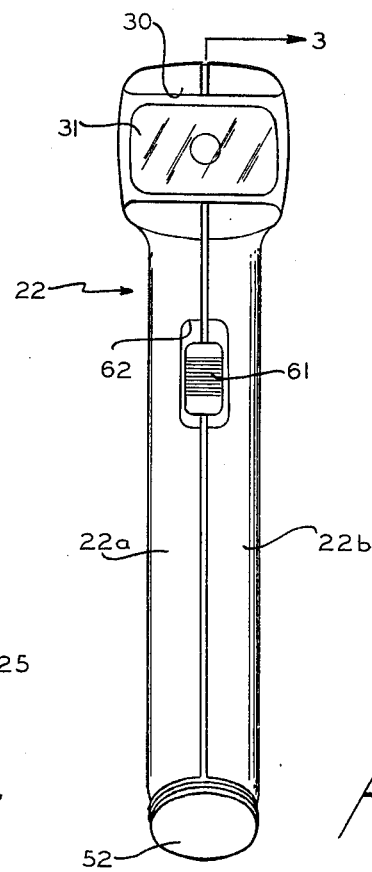
FIG. 2 is a rear elevation of the otoscope of FIG. 1.

When the lens 31 is positioned so as to close the opening 30 in the proximal side of the instrument head portion 24 as shown in FIGS. 1–3, it engages the rear side of gasket 42 in an airtight manner. Since the speculum 27 also engages the walls of the ear canal in a substantially airtight manner, this enables air under low pressure to be introduced into the ear through a hole 47 in the inner form 32, FIG. 8, the hole registering with a hole (not shown) in the body half 22b. The air is supplied by a pneumatic attachment (not shown) of the type disclosed in U.S. Pat. No. 3,698,387, the attachment comprising a compressible inflation bulb having a tube that is inserted in the hole 47.

The light source unit 26, FIGS. 3–7, is releasably secured in the handle portion 25 of the instrument and includes an upstanding molded plastic support member 48 in which batteries 50a, 50b and a lamp 51 are mounted. The base 52 of the member serves as a closure for the lower end of the handle and also as a means for grasping the light source unit to withdraw it from the handle. The batteries 50a and 50b are received in recesses 53, FIG. 7, on opposite sides of the support member and are releasably retained in position by the ends of a spring metal conductor strip 54, FIGS. 4 and 5, which connects the positive terminal of battery 50a with the negative terminal of battery 50b.

The lamp 51 is positioned in a socket 55 at the upper end of the support member 48. The socket is smooth bored and the lamp is releasably retained therein by one end of a spring metal conductor strip 56, FIGS. 4 and 5. The negative terminal of battery 50a is connected to the base terminal of the lamp by a spring metal conductor strip 57. The circuit through the batteries and lamp is completed by a spring metal conductor strip 58 in contact with the positive terminal of battery 50b and a switch 60, FIG. 3, which in its ON position bridges conductor strips 56 and 58.

The switch 60 is a molded plastic member that has a portion 61 which projects outwardly through an opening 62, FIGS. 2 and 3, in the instrument body to permit manual operation of the switch. On its inner side, the switch carries an elongated metal plate having tab extensions 64. The lower tab extension engages conductor strip 58, FIGS. 3 and 5, at all times while the upper tab extension either rests in a notch 65 in the support member 48 when the switch is in its lower, OFF position or engages the conductor strip 56 when the switch is moved upwardly to its ON position. With the switch 60 in its ON position, a circuit is completed from the positive terminal of battery 50a, through conductor strip 54, battery 50b, conductor strip 58, the switch, conductor strip 56, the lamp 51 and conductor strip 57 back to the negative terminal of battery 50a.

Figures 4, 5, 6, 7:
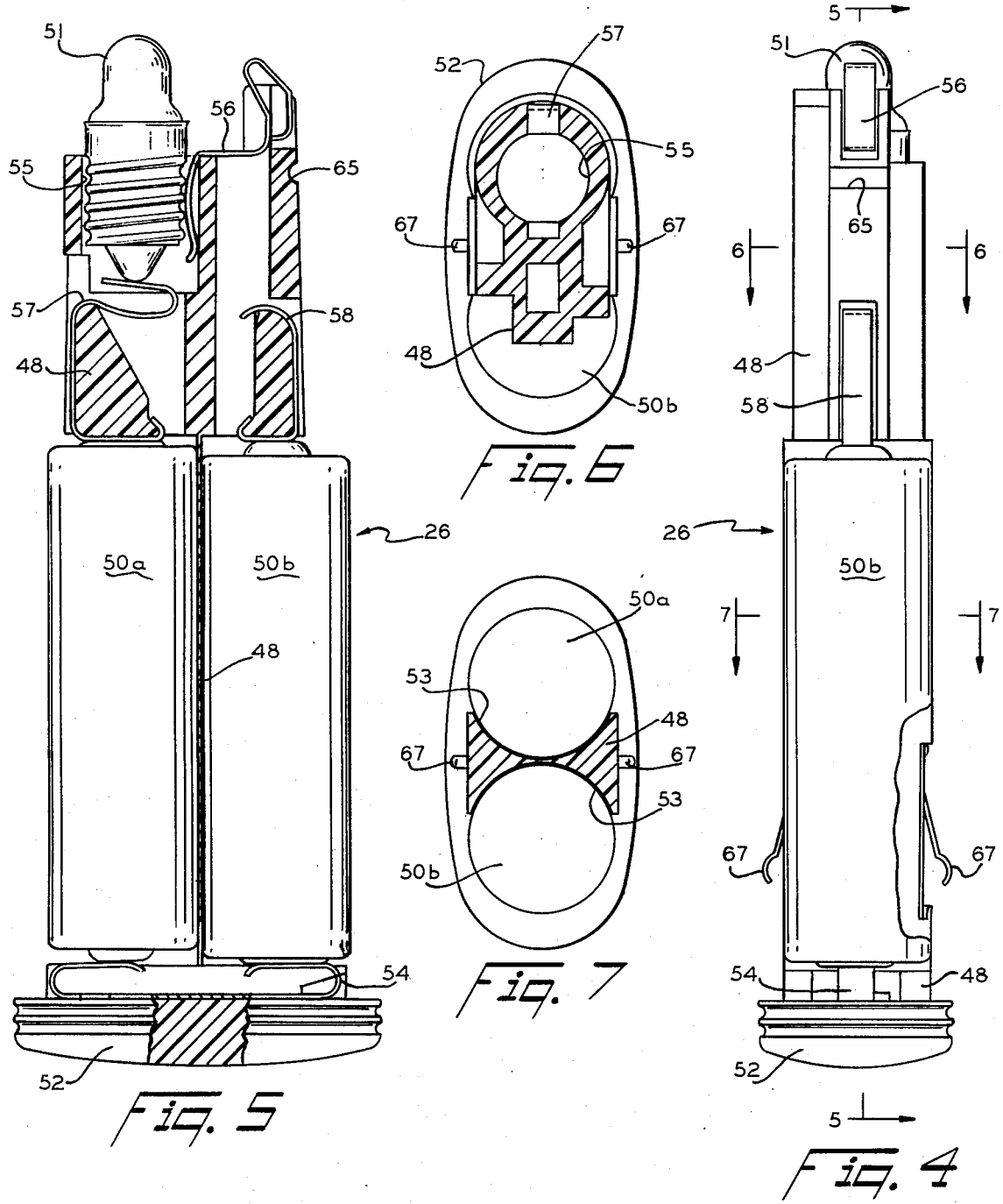
FIG. 4 is an enlarged rear elevation of the removable light source unit of the otoscope.
FIG. 5 is a vertical section through the light source unit taken on line 5—5 of FIG. 4.
FIGS. 6 and 7 are horizontal sections through the light source unit taken on lines 6—6 and 7—7, respectively, of FIG. 4.

As shown in FIG. 5, conductor strip 57 is bent back upon itself at the base of the lamp so as to form a spring that operates to bias the lamp out of the socket, or upwardly as viewed in FIG. 5. This spring bias coacts with a U-shaped bracket 66, FIG. 3, formed on the inside wall of the body half 22b to insure that the lens end of lamp 51 will always be brought into engagement with the bracket and thus be properly aligned with the lower end 35 of the fiber optic bundle regardless of any minor dimensional variations.

The light source unit 26 is releasably retained in the handle portion of the instrument by outwardly projecting spring tabs 67, FIGS. 3 and 4, on opposite sides of the support member 48. The lower, rounded ends of these tabs extend into shallow recesses (not shown) in the body halves 22a and 22b but can be forced out of the recesses upon the application of a moderate force to the base 52 of the support member.

Having reference now to FIGS. 10–19, the ophthalmoscope embodying the invention includes an elongated hollow body, generally indicated at 70, formed of two mating halves 70a and 70b of molded plastic. The body has an upper head portion 71 and a lower handle portion 72, the handle portion being open at its lower end to allow a light source unit generally indicated at 74 to be inserted therein. The unit 74, which is very similar to the otoscope light source unit 26, includes the light source and power supply for the instrument as will be explained.

The head portion 71 of the instrument body has a horizontal viewing passage therethrough with an aperture 75, FIG. 12, on its front or distal side that is brought close to the patient's eye and a smaller aperture 76, FIGS. 11 and 12, on its rear or proximal side into which the physician looks. The scalloped edge of a lens wheel 77 is accessible on opposite sides of the instrument to permit the wheel to be turned to bring a lens with the desired focal length into registry with the aperture 76. A second aperture 78 on the proximal side of the instrument is for viewing identifying indicia for the lens in registry with the viewing passage as is conventional in ophthalmoscopes.

Referring to FIG. 12, the light source unit 74 includes a lamp 80, and the light rays from this lamp pass upwardly through a condensing lens 81, through an aperture slide assembly 82 to be described, and then through an objective lens 84 to an obliquely disposed mirror 85. The mirror alters the direction of the light rays so that they are directed out through the aperture 75 into the eye of the patient. The physician looks through aperture 76, through the selected lens in lens wheel 77 and over the top edge of mirror 85 into the illuminated area of the patient's eye.

The aperture slide assembly 82, FIGS. 12, 15 and 19 is positioned just above the condensing lens and is mounted in the instrument for horizontal sliding movement as indicated by the arrow 86 in FIG. 15. The assembly is formed with a substantially vertical wall 87 and a substantially horizontal wall 88 that extends rearwardly from the lower edge of the vertical wall. In FIG. 19, the assembly is inverted from its position in the instrument as shown in FIGS. 12 and 15.

On its front side, the vertical wall 87 of the assembly has a projection 90 that extends outwardly through an aperture 91 in the body half 70b to permit the assembly to be moved manually to the position desired. Between the front side of wall 87 and the interior wall of body half 70b there is a resilient gasket 92 to prevent dust and dirt from entering the instrument through the aperture 91. In the horizontal wall 88 of the slide assembly there are two circular apertures 94, 95 of different diameters and a grid aperture 96. The slide assembly can be moved to position one of these apertures in registry with the condensing lens 81 thereby giving the physician a choice as to the size of the illuminated spot in the patient's eye or as to use of the grid.

The slide assembly is formed with notches 97, FIG. 19, at its lower front edge. These are opposite the three apertures 94, 95 and 96, and when the selected aperture is in registry with the condensing lens a spring biased ball detent 98, FIG. 12, enters the corresponding notch to releasably hold the slide assembly in position.

The aperture slide assembly 82 is held in position against the gasket 92 by an insert support member 101, FIGS. 12 and 18. The insert support member is a unitary molded plastic element that fulfills several different functions. Thus, the support member has a circular boss 102, FIGS. 17 and 18, on which the lens wheel 77 is rotatably mounted. Above the boss 102 on the same side, the support member is formed with a lug 104 that supports a spring strip detent 105, the rounded free end of which engages the scalloped edge of the lens wheel to releasably retain it in a selected position, FIGS. 12 and 16.

Below the boss 102, the support member 101 is formed with a protuberance 106, FIGS. 17 and 18, over which a metal plate 107 is snapped. The plate has a downwardly projecting spring contact finger 108 which contacts the side terminal of the lamp 80 as shown in FIG. 12 to form a part of the electrical circuit to be described. On its side opposite the boss 102, the support member is formed with a projection 110 having a triangular cross-section and this projection provides back-up for the mirror 85 as shown in FIG. 12.

The lens wheel 77 is a unitary molded plastic element, FIG. 16, wherein the lenses 111 of different focal lengths are simultaneously formed when the wheel is molded. The numbers or other identifying indicia 112 for the lenses lie on an inner circle concentric with the circle of lenses, the indicia for each lens being diametrically opposite the lens so that when the latter registers with the aperture 76 its indicia will appear in the aperture 78, FIGS. 11 and 12. Aperture 78 is provided with a magnifier lens 113 to facilitate reading the identifying indicia.

As noted above, the light source unit 74, FIGS. 12–14, of the ophthalmoscope is very similar to the otoscope light source unit 26. Thus, the unit 74 is normally releasably retained in the ophthalmoscope handle portion 72 by outwardly projecting spring tabs 114, FIG. 13, which extend into shallow recesses (not shown) in the instrument body halves. Unit 74 includes an upstanding molded plastic support member 115 which carries batteries 116a and 116b and the lamp 80. The base 117 of the support member serves as a closure for the lower end of the handle and also as a means for grasping the unit to withdraw it.

The lamp 80 is positioned in a smooth bore socket 118 at the upper end of support member 115 and is releasably held therein by the coaction of a pin 120 on the lamp and a bayonet slot 121 in the support member as indicated in FIG. 14. Lamp 80 is biased outwardly in socket 118 by a spring metal conductor strip 122 which also connects the base terminal of the lamp with the positive terminal of battery 116b.

The switch for the lamp-battery circuit is best shown in FIG. 12 and comprises a molded plastic member 124 that has a portion 125 which projects out through an aperture 126 in the instrument body to permit manual operation of the switch. On its inner side, the switch carries an elongated metal plate having tab extensions 128. The lower tab extension engages a metal conductor strip 130 at all times while the upper tab extension either rests in a notch 131 in the previously described protuberance 106 on support member 101 when the switch is in its lower, OFF position or engages the spring contact finger 108 when the switch is moved upwardly to its ON position. With the switch 124 in its ON position, FIGS. 12–14, a circuit is completed from the positive terminal of battery 116a, through a spring metal conductor strip 132, battery 116b, conductor strip 122, lamp 80, contact finger 108, the switch and conductor strip 130 back to the negative terminal of battery 116a.

The construction and arrangement of the ophthalmoscope just described is particularly advantageous in enabling the instrument to be quickly and easily assembled. Thus, starting with the two instrument body halves 70a and 70b apart, the condensing lens 81, the objective lens 84 and mirror 85 are placed in slots formed in the interior of body half 70b as best shown in Fig. 15. Thereafter, the gasket 92 and aperture slide assembly 82 are dropped into position with the body half resting in a horizontal position on a work surface.

The insert support member 101 with metal plate 107 already mounted on protuberance 106, FIG. 18, is then positioned in body half 70b so that it contacts the slide assembly 82 and triangular projection 110 engages the back of mirror 85. The support member 101 fits between a pair of parallel walls 134, FIGS. 15 and 16, formed in the interior of the body half 70b and is retained in position by the frictional engagement of its edges with these walls. The lens wheel 77 and spring detent 105 are then mounted on the support member as shown in FIG. 16.

After the components have been assembled in body half 70b as above described, the switch 124 and magnifier lens 113 are mounted in body half 70a and the two halves with the components therein are sonic welded together at their mating edges. Thereafter, the light source unit 74 with the lamp and batteries mounted in it is inserted in the handle portion 72 to complete the assembly of the instrument.

For good performance of the instrument, it is important that the lens of lamp 80 be precisely positioned with respect to the condensing lens 81. To this end, the lamp is received with a close fit between a pair of walls 135, FIGS. 12 and 15, when the light source unit is inserted in the instrument handle. The walls serve to properly locate the lamp with respect to the lens and the spring strip 122, FIG. 14, below the lamp compensates in the longitudinal direction for any minor dimensional variations.

As previously indicated, the easy removal of the light source unit 74 as a unit is advantageous in that it greatly facilitates changing the batteries and/or the lamp and none of the optical components need be interfered with.

From the foregoing description, it will be apparent that the invention provides a novel and very desirable construction for electrically illuminated medical diagnostic instruments. As will be understood by those familiar with the art, the invention may be embodied in other specific forms without departing from the spirit or essential characteristics thereof.

We claim:

1. In an electrically illuminated medical diagnostic instrument, an elongated hollow body formed of two mating halves, the body having an upper head portion and a lower handle portion, optical means in the instrument body for directing light rays from a light source normally concealed in the interior of the body to a point in the head portion removed from the light source from which the rays are directed outwardly toward the area to be examined, and a light source unit mounted in the handle portion of the body, the unit including a light source in the form of a lamp and means for supplying power to the lamp, means supporting the lamp and power supply means as to be removable as a unit from the handle portion to permit access to the parts of the unit for replacement.

2. The combination defined in claim 1 wherein the instrument is an ophthalmoscope and the optical means includes lenses and a mirror.

3. The combination as defined in claim 1 wherein the instrument is an otoscope and the optical means comprises clad optical fibers.

4. An electrically illuminated medical diagnostic instrument comprising an elongated hollow body formed of two mating halves, the body having an upper head portion and a lower handle portion, the handle portion having an access opening at its lower end; optical means in the instrument body for directing light rays from a lamp normally positioned in the body to a point in the head portion thereof removed from the light source from which the rays are directed outwardly toward the area to be examined; a light source unit removably mounted in the handle portion of the body by being inserted in said opening, the unit including an upstanding support member and battery means and a lamp carried by the support member, the lower end of the support member forming a closure for the lower end of the handle portion when the light source unit is mounted therein, the light source unit having an open electrical circuit between its lamp and battery means; and a switch in the instrument body operable to complete the circuit when the light source unit is mounted in the body.

5. The combination defined in claim 4 wherein the instrument is an ophthalmoscope and the optical means includes lenses and a mirror.

6. The combination defined in claim 4 wherein the instrument is an otoscope and the optical means comprises clad optical fibers.

* * * * *